(12) United States Patent
Mormile et al.

(10) Patent No.: US 9,328,360 B2
(45) Date of Patent: May 3, 2016

(54) CONVERSION OF GLYCEROL TO 1,3-PROPANEDIOL UNDER HALOALKALINE CONDITIONS

(71) Applicant: The Curators of the University of Missouri, Columbia, MO (US)

(72) Inventors: Melanie Rose Mormile, Rolla, MO (US); Daniel William Roush, Chandler, AZ (US); Dwayne Alexander Elias, Knoxville, TN (US); Oliver Clifford Sitton, Rolla, MO (US)

(73) Assignee: The Curators of the University of Missouri, Columbia, MO (US)

(*) Notice: Subject to any disclaimer, the term of this patent is extended or adjusted under 35 U.S.C. 154(b) by 0 days.

(21) Appl. No.: 14/479,292

(22) Filed: Sep. 6, 2014

(65) Prior Publication Data

US 2015/0072388 A1 Mar. 12, 2015

Related U.S. Application Data

(60) Provisional application No. 61/874,752, filed on Sep. 6, 2013.

(51) Int. Cl.
*C12P 7/18* (2006.01)

(52) U.S. Cl.
CPC ........................................ *C12P 7/18* (2013.01)

(58) Field of Classification Search
None
See application file for complete search history.

(56) References Cited

U.S. PATENT DOCUMENTS 5,686,276 A * 11/1997 Laffend et al. ................ 435/158
7,582,457 B2 9/2009 Dunn-Coleman et al.
8,034,592 B2 * 10/2011 Elias et al. .................... 435/168
2003/0022323 A1 1/2003 Dunn-Coleman et al.
2010/0028965 A1 2/2010 Liu et al.
2011/0136196 A1 * 6/2011 Elias et al. .................... 435/168
2013/0177956 A1 7/2013 Figge

OTHER PUBLICATIONS

Kivisto et al., Journal of Biotechnology 158:242-247, available online Nov. 6, 2011.*
Brown et al., Genbank accession No. CP002304, 2011.*
The 2012 ATCC catalog.*
Van Gerpen, J., Improvement of Crop Plants for Industrial End Uses, Chapter 10, pp. 281-289, P. Ranalli Editor, 2007.*
Cayol et al., Extremophiles 6:131-134, 2002.*
Croft et al., Nature 438:90-93, 2005.*
Ohwada et al., Limnology and Oceanography 17(2):315-320, 1972.*
Kivisto et al., Bioresource Technology 101:8671-8677, 2010.*
Kivisto et al., "Non-sterile process for biohydrogen and 1,3-propanediol production from raw glycerol," International Journal of Hydrogen Energy, Jul. 26, 2013, vol. 38, Issue No. 27, 11749-11755.
International Search Report and Written Opinion mailed Dec. 23, 2014 in corresponding PCT/US2014/054434 filed Sep. 6, 2014.
Brown et al., "Complete Genome Sequence of the Haloalkaliphilic, Hydrogen-Producing Bacterium Halanaerobium hydrogeniformans," Journal of Bacteriology, Jul. 2011, vol. 193, No. 14, 3682-3683.
Kivisto et al., "Halophilic anaerobic fermentative bacteria," Journal of Biotechnology 152 (2011) 114-124.
McAdams et al., "Stochastic mechanisms in gene expression", Proc. Natl. Acad. Sci. USA 94 (1997) 814-819, vol. 94.

* cited by examiner

*Primary Examiner* — Delia Ramirez
(74) *Attorney, Agent, or Firm* — Hovey Williams LLP

(57) ABSTRACT

A method of producing 1,3-propanediol. The method comprises fermenting a haloalkaliphilic species of *Halanaerobium* with a source of glycerol into 1,3-propanediol, at a pH of greater than about 10 and at a salt concentration of greater than about 5% w/v. Furthermore, with supplementation of vitamin $B_{12}$, the yield of 1,3-propanediol to glycerol can be increased.

20 Claims, 6 Drawing Sheets

Peak Height = 281 + 536 Conc
Conc = (Peak Height − 281) / 536
$R^2$ = 99.9% Adj.| $R^2$ =99.9% | P-value = <0.001

Peak Area = 4617 + 9403 Conc
Conc = (Peak Height − 4617) / 9403
$R^2$ = 99.9% Adj.| $R^2$ =99.9% | P-value = <0.001

Peak Height = 180 + 350 Conc. (mM)
Conc = (Peak Height − 180) / 350
$R^2$ = 99.9% Adj.| $R^2$ =99.8% | P-value = <0.001

Peak Area = 4492 + 7661 Conc. (mM)
Conc = (Peak Height − 4492) / 7661
$R^2$ = 99.8% Adj.| $R^2$ =99.7%| P-value = <0.001

CONVERSION OF GLYCEROL TO 1,3-PROPANEDIOL UNDER HALOALKALINE CONDITIONS

CROSS-REFERENCE TO RELATED APPLICATIONS

The present application claims the priority benefit of U.S. Provisional Patent Application Ser. No. 61/874,752, filed Sep. 6, 2013, entitled CONVERSION OF GLYCEROL TO 1,3-PROPANEDIOL UNDER HALOALKALINE CONDITIONS, incorporated by reference in its entirety herein.

SEQUENCE LISTING

The following application contains a sequence listing in computer readable format (CRF), submitted as a text file in ASCII format entitled "SequenceListing," created on Aug. 28, 2014, as 20 KB. The content of the CRF is hereby incorporated by reference.

BACKGROUND

1. Field of the Invention

This invention will provide a way for biodiesel companies to form a valuable product, (1,3-propanediol) from a waste product (glycerol).

2. Description of Related Art

Chemical waste can be recycled into useful compounds. With the recent surge in biodiesel production, glycerol has gone from a relatively rare commodity to a heavily overproduced waste product. Many major chemical and agriculture companies have been attempting to find high yielding conversions for glycerol. One of the major processes is the conversion of glycerol into 1,3-propanediol by way of microbial metabolism. There has been success in identifying strains of microorganisms that can conduct this reaction; however it may not be commercially feasible as the raw glycerol product needs to be treated. For economic feasibility, the process must be able to convert the raw glycerol product into 1,3-propanediol with limited treatment. For example, 1,3-propanediol, is used frequently in the chemical industry as a building block for many common products, like adhesives, fragrances and perfumes, personal care products, and coatings like paint. Currently, 1,3-propanediol is synthesized from components of crude oil, propylene or ethylene oxide, or glucose derived from corn to synthesize. However, common chemical processes for recycling chemical waste involve making the processing streams more tolerable to bacteria for biological conversion. By adding large amounts of acids or bases, or using large amounts of energy to remove salts and impurities, industries make the conditions suitable for non-extremophilic life. Glycerol is another common waste product of biodiesel production that can be converted into useful compounds. With the recent surge in biodiesel production, glycerol has gone from a relatively rare commodity to a heavily overproduced waste product. Many major chemical and agriculture companies have been attempting to find high yielding conversions for glycerol. One of the major process targets is the conversion of glycerol into 1,3-propanediol by way of microbial metabolism (FIG. 1). There has been success in identifying strains of microorganisms that can conduct this reaction; however it may not be commercially feasible as the raw glycerol product needs to be treated. Glycerol acts very much like salt, in the sense that it increases the pressure put onto the bacteria. For economic feasibility, the process must be able to convert the raw glycerol product into 1,3-propanediol with limited treatment. Accordingly, there remains a need for improved approaches to converting chemical waste into useful compounds and products.

SUMMARY OF THE INVENTION

The invention addresses the problems above by providing a method of producing 1,3-propanediol. The method comprises fermenting a species of *Halanaerobium* with a source of glycerol, whereby 1,3-propanediol is produced. Fermentation can be carried out under high pH and high salt concentrations, and without the removal of impurities from the glycerol feedstock. Fermentative conversion rates can be increased by supplementing the fermentation culture with vitamin $B_{12}$.

DETAILED DESCRIPTION OF THE PREFERRED EMBODIMENTS

Figure 1:
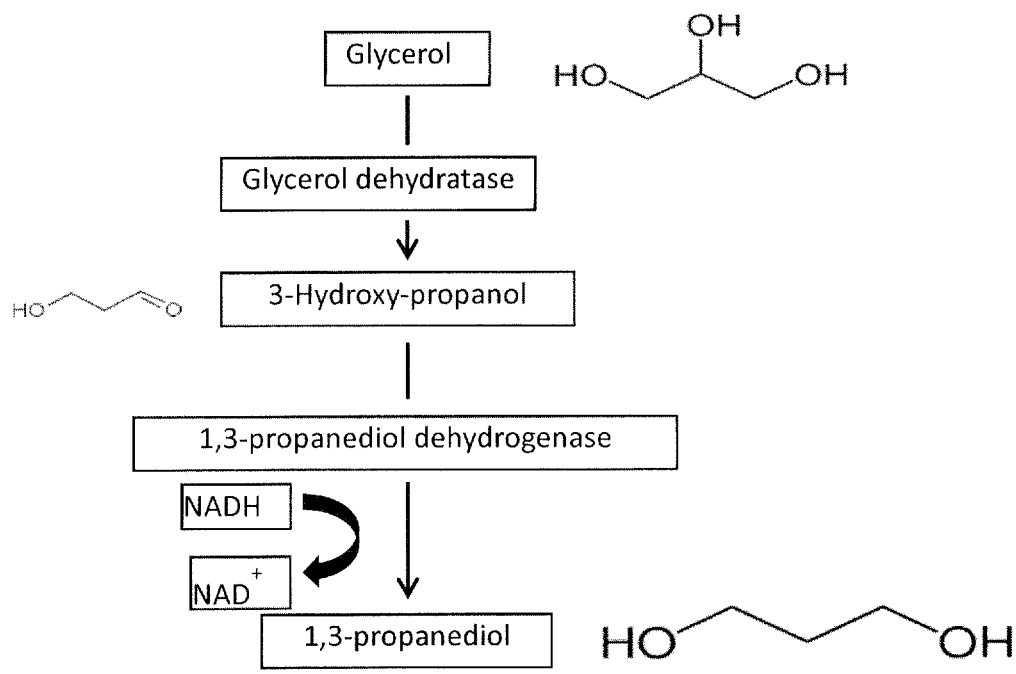
FIG. 1 illustrates the process of converting glycerol to 1,3-propanediol.

The present invention provides a process for the fermentative production of 1,3-propanediol without the currently required steps of pretreating, desalination, or the neutralization to decrease the salinity or pH of the feedstock or fermentation media, or remove waste by-products typically present in the crude feedstock. The inventive process is amenable to larger scale, commercial or industrial applications for the production of 1,3-propanediol as a useful precursor material from microbial fermentation of chemical waste, and specifically a chemical waste feedstock comprising glycerol or a source of glycerol in an inexpensive and environmentally friendly manner.

The inventive methods utilize extremophilic microorganisms that can thrive in the presence of untreated chemical waste. Specifically the preferred organism, *Halanaerobium hydrogeniformans* (ATCC Patent Deposit Designation No. PTA-10410, deposited Oct. 13, 2009), grows in conditions with high pH (about pH 11 which is similar to laundry detergent) and high salt concentrations (7% salt, double that of the ocean). These conditions are found in treated biomass used to produce biofuels like ethanol and hydrogen, and crude glycerol generated during biodiesel production.

Fermentation of the chemical waste feedstock is accomplished with a haloalkaliphilic microorganism capable of 1,3-propanediol production under highly alkaline and hypersaline conditions. *H. hydrogeniformans* is able to convert glycerol, a common waste product of biodiesel production, into 1,3-propanediol under extreme conditions, of pH 11 and 7% salt. In preferred embodiments, a conversion rate of about 55% can be achieved with the process. Advantageously, the microorganism can also grow in media containing up to 1M glycerol and can thrive in a solution containing crude waste glycerol.

Unlike other members of the *Halanaerobium* genus, the microorganism is highly alkaliphilic with optimum growth at a pH of from about 10.5 to about 11. Suitable microorganisms for use with the inventive method preferably have a 16S ribosomal DNA (rDNA) sequence comprising (or consisting of) SEQ ID NO: 1, or a 16S rDNA sequence having at least 98% sequence homology with SEQ ID NO: 1, and more preferably at least 99% sequence homology with SEQ ID NO: 1. Suitable microorganisms will preferably have at least one gene encoding for glycerol dehydratase or an enzyme having glycerol dehydratase activity, and preferably an endogenous gene encoding for glycerol dehydratase or an enzyme having glycerol dehydratase activity. In one or more embodiments, the microorganisms comprise an endogenous DNA sequence comprising (or consisting of) SEQ ID NO:2 or a sequence having at least 98% sequence homology with SEQ ID NO: 2, and more preferably at least 99% sequence homology with SEQ ID NO: 2. In one or more embodiments, the microorganisms comprise a gene encoding for an endogenous protein comprising (or consisting of) SEQ ID NO:3, or a sequence having at least 98% sequence homology with SEQ ID NO: 3, and more preferably at least 99% sequence homology with SEQ ID NO: 3.

Suitable microorganisms will preferably have at least one gene encoding for iron-containing alcohol dehydrogenase or an enzyme having alcohol dehydrogenase activity, and preferably an endogenous gene encoding for iron-containing alcohol dehydrogenase or an enzyme having alcohol dehydrogenase activity. In one or more embodiments, the microorganisms comprise an endogenous DNA sequence comprising (or consisting of) SEQ ID NO:4 or a sequence having at least 98% sequence homology with SEQ ID NO: 4, and more preferably at least 99% sequence homology with SEQ ID NO: 4. In one or more embodiments, the microorganisms comprise a gene encoding for an endogenous protein comprising (or consisting of) SEQ ID NO:5, or a sequence having at least 98% sequence homology with SEQ ID NO: 5, and more preferably at least 99% sequence homology with SEQ ID NO: 5. In one or more embodiments, the microorganisms comprise an endogenous DNA sequence comprising (or consisting of) SEQ ID NO:6 or a sequence having at least 98% sequence homology with SEQ ID NO: 6, and more preferably at least 99% sequence homology with SEQ ID NO: 6. In one or more embodiments, the microorganisms comprise a gene encoding for an endogenous protein comprising (or consisting of) SEQ ID NO:7, or a sequence having at least 98% sequence homology with SEQ ID NO: 7, and more preferably at least 99% sequence homology with SEQ ID NO: 7. Suitable microorganisms include mutants and derivatives (progeny) of the microorganism which retain the haloalkaliphilic properties *H. hydrogeniformans*. Mutants (such as by deletion, insertion, and/or substitution of a base in the above-referenced sequences) include those occurring spontaneously in the passage or cultivation of the organism, as well as intentional mutations. In one or more embodiments, haloalkaliphilic microorganisms can also be used, which have been engineered to contain one or more of the genes referenced above or a gene encoding for one or more of the enzymes referenced above.

The chemical waste feedstock comprising glycerol or a source of glycerol is fermented with the microorganism in a culture medium under conditions suitable for 1,3-propanediol production. A preferred culture medium comprises, consists essentially, or even consists of (per liter): 70 g NaCl, 40 g $Na_2CO_3$, 6.3 g $K_2HPO_4$, 1 g yeast extract, 0.75 g $Na_2S$, and 0.6 g cysteine, along with 10 ml of basal medium stock solution and 10 ml of trace mineral solution. The basal medium stock solution preferably comprises 50 mg $NH_4NO_3$, 8.5 mg $MgCl_2.6H_2O$, 7.5 mg $SiO_2$, 4.5 mg $MnSO_4.H_2O$, 4.2 mg $CaCl_2.2H_2O$, 4 mg methylene blue, and 1.8 mg $FeSO_4.7H_2O$. The trace mineral solution preferably comprises (per liter): 3 g $MgSO_4.7H_2O$, 1.63 g $Na_3$-NTA, 1 g NaCl, 0.64 g $MnCl_2.4H_2O$, 0.13 g $ZnCl_2$, 0.1 g $FeSO_4.7H_2O$, 0.1 g $CaCl_2.2H_2O$, $CoCl_2.6H_2O$, 0.03 g $NiSO_4.6H_2O$, 0.025 g $Na_2Mo_4.2H_2O$, 0.025 g $Na_2WO_4.2H_2O$, 0.01 g AlK$(SO_4)_2.12H_2O$, 0.01 g $H_3BO_3$, and 7 mg $CuCl_2.2H_2O$.

The chemical waste feedstock comprising glycerol or the glycerol source is preferably provided at a glycerol concentration of from about 1 g/L to about 184 g/L, and preferably from about 10 g/L to about 92 g/L. The microorganism can ferment feedstocks with a glycerol concentration as high as 184 g/L. The microorganism ferments the feedstock to generate 1,3-propanediol along with other by-products.

As mentioned, the method is preferably carried out without neutralization of the chemical waste feedstock (i.e., without decreasing the pH to about 7). That is, the pH of the feedstock (and resulting fermenting culture, including the culture media) is preferably greater than or equal to about 10, preferably from about 10 to about 11, and more preferably from about 10.5 to about 11. The salinity (% NaCl content) of the feedstock and fermenting culture (including the culture media) is also preferably greater than or equal to about 5% w/v, more preferably greater than or equal to about 7% w/v, and even more preferably from about 7% to about 7.5% w/v. As used herein, the percentage "weight by volume" of the component in the composition (referred to herein as "% w/v") is calculated based upon the total mass of the component (e.g., salt) in grams per liter of the final solution where 1000 g/L is taken as 100% w/v. These pH and salinity conditions are preferably maintained in the culture medium throughout the fermentation process. That is, the pH of the fermenting culture preferably remains at or above about pH 10, and more preferably from about 10.5 to about 11, while the salinity remains greater than or equal to about 5% w/v, preferably greater than or equal to 7% w/v, and more preferably from about 7% to about 7.5% w/v.

Preferably, the feedstock is not purified or pretreated. In one or more embodiments, the feedstock will also comprise methanol, crude glycerol, sodium hydroxide, water, and mixtures thereof. Methanol is commonly present in the biodiesel waste stream along with glycerol. Advantageously, the microorganism has a tolerance to raw biodiesel waste. Accordingly, in one or more embodiments, such impurities or chemicals are not removed from the feedstock prior to fermentation. The microorganism is expected to form 1,3-propanediol from the glycerol in untreated biodiesel waste, which will save producers from having to remove methanol and other possible contaminants that would typically inhibit less tolerant fermentative bacteria.

In one or more embodiments, the fermentation culture is preferably supplemented with vitamin $B_{12}$. Preferably, vitamin $B_{12}$ is present in the fermentation culture at a level of from about 25 µg/L to about 100 µg/L, more preferably from about 25 µg/L to about 75 µg/L, and even more preferably from about 25 µg/L to about 50 µg/L. Advantageously, the endogenous glycerol dehydratase of *H. hydrogenoformans* is not necessarily dependent on $B_{12}$, and can ferment glycerol to 1,3-propanediol without $B_{12}$ supplementation. However, it has been shown that $B_{12}$ can enhance the yield, as much as 0.47 (mol/mol).

In one or more embodiments, fermentation is preferably carried out under substantially anaerobic conditions. As used herein, "substantially anaerobic conditions" refers to conditions where there no free oxygen available (e.g., less than about 0.1 ppm free oxygen, preferably from about 0 to about 0.1 ppm free oxygen), and includes naturally or artificially oxygen-depleted environments. More preferably, for artificial environments (i.e., test tube, fermentation reactor) a gas phase is provided in the headspace above the culture medium, with suitable gases being selected from the group consisting of $N_2$, $CO_2$, and mixtures thereof. A particularly preferred gas phase is a combination of about 80% $N_2$/20% $CO_2$. In a preferred method, the substantially anaerobic conditions can be maintained by sparging the culture medium with the selected gases.

The culture medium is also preferably agitated during fermentation, preferably at speeds of from about 100 rpm to about 250 rpm, and more preferably from about 100 rpm to about 200 rpm. Agitation can be accomplished via shaking, rotation, impeller, or any combination thereof. Fermentation also preferably proceeds in the absence of light (i.e., the culture is not exposed to any light sources during the fermentation process). Fermentation is preferably carried out at a temperature of from about 6° C. to about 40° C., and preferably from about 25° C. to about 30° C., and for time periods of from about 12 hours to about 72 hours, and preferably for time periods of from about 12 hours to about 24 hours.

The fermentation process preferably results in a percent mole/mole yield of 1,3-propanediol from glycerol of at least about 32% with a glycerol-only medium, and preferably from about 32% to about 60% and a theoretical yield over 90%. With a vitamin $B_{12}$ amended medium, the yield of 1,3-propanediol from glycerol is preferably greater than about 60%, and preferably from about 60% to about 80% and a theoretical yield over 90%, The yield is calculated by:

$$\frac{\text{(mol 1,3-propanediol produced)}}{\text{(mol glycerol initial)}} = \text{Yield}$$

or $$\frac{\text{(mol 1,3-propanediol produced)}}{\text{(mol glycerol initial with added } B_{12})} = \text{Yield}$$

In one or more embodiments, the process has a yield of 1,3-propanediol of about 60% at about pH 11 and a media containing about 7% salt and about 0.2% glycerol, with added $B_{12}$.

Fermentation can be carried out in a fermentation apparatus (fermentation reactor). Suitable fermentation reactors are known in the art. In general, suitable apparatuses will have inlets for the biodiesel waste feedstock, gas for artificial atmosphere, and a fermentation chamber, and outlets for removing the 1,3-propanediol and by-products. The apparatus will contain the microorganism and nutrient culture medium. The apparatus can also be equipped with a stir bar, impeller or other agitation device. The feedstock may be continuously supplied to the fermentation apparatus as needed to keep up with the rate of fermentation of the chemical waste substrate. The fermentation apparatus may be a stand-alone apparatus, or it may be combined with a downstream reactor for receiving and further processing any by-products from the fermentation apparatus.

The process further comprises recovering the produced 1,3-propanediol from the fermentation reaction. The resulting 1,3-propanediol can be separated from the fermentation culture, such as by distillation, extraction, or other separation method.

In yet a further embodiment, the waste stream from the fermentation reactor is recycled and reintroduced into the system. This is feasible in the inventive process because the salt concentration and pH of the waste stream would still be amenable to microbial cultivation using the extremophilic microorganism. The pH or salt concentration may be adjusted (upwards), if necessary. Advantageously, this significantly reduces not only the amount of water required for the process, but the cost of the substrates for the cultivation and thereby the overall cost of the production of 1,3-propanediol.

The benefits and novelty of our process is that the microorganism can convert glycerol to 1,3-propanediol under alkaline conditions without the need to neutralize the raw glycerol to a pH value of 7.0. In addition, the microorganism is halo-tolerant and can withstand saline conditions. Typically, raw glycerol wastes have a salinity of ~5%. With the microorganism, there is no need to dilute the residual salt in the waste. The use of the microorganism will help to streamline the process of glycerol conversion to 1,3-propanediol. The competitive advantage is that the biodiesel waste stream will not have to be treated to remove the salts or adjust its pH.

Additional advantages of the various embodiments of the invention will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described herein.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

EXAMPLES

The following examples set forth methods in accordance with the invention. It is to be understood, however, that these examples are provided by way of illustration and nothing therein should be taken as a limitation upon the overall scope of the invention.

Example 1

*Halanaerobium hydrogeniformans*

Figure 2:
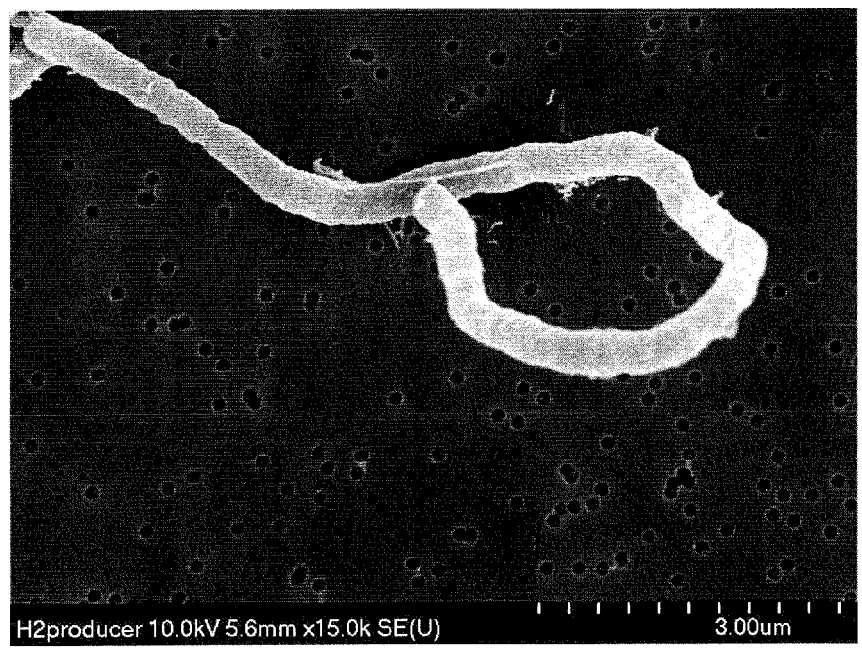
FIG. 2 is a scanning electron microscope (SEM) photograph of the haloalkaliphilic species of *Halanaerobium*.
Figure 3:
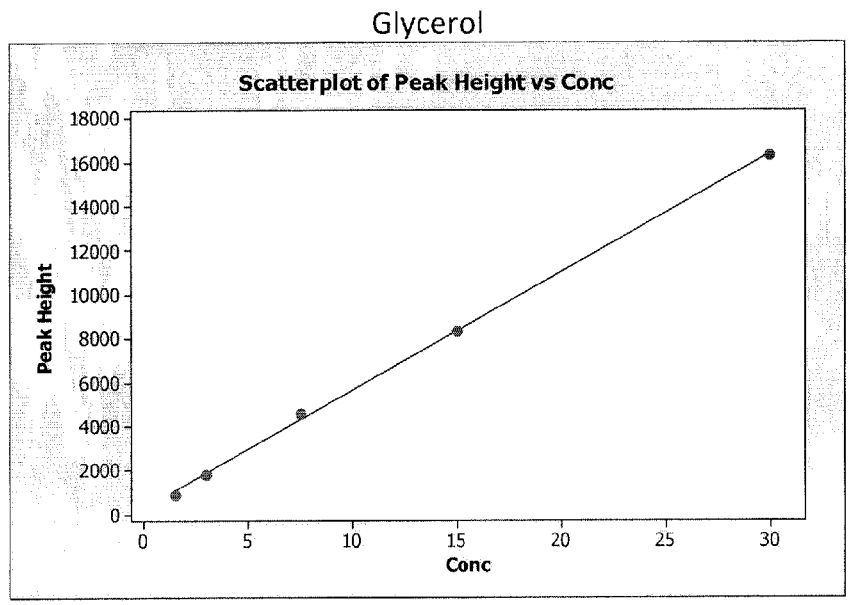
FIG. 3 is a scatterplot graph of glycerol consumption.
Figure 4:
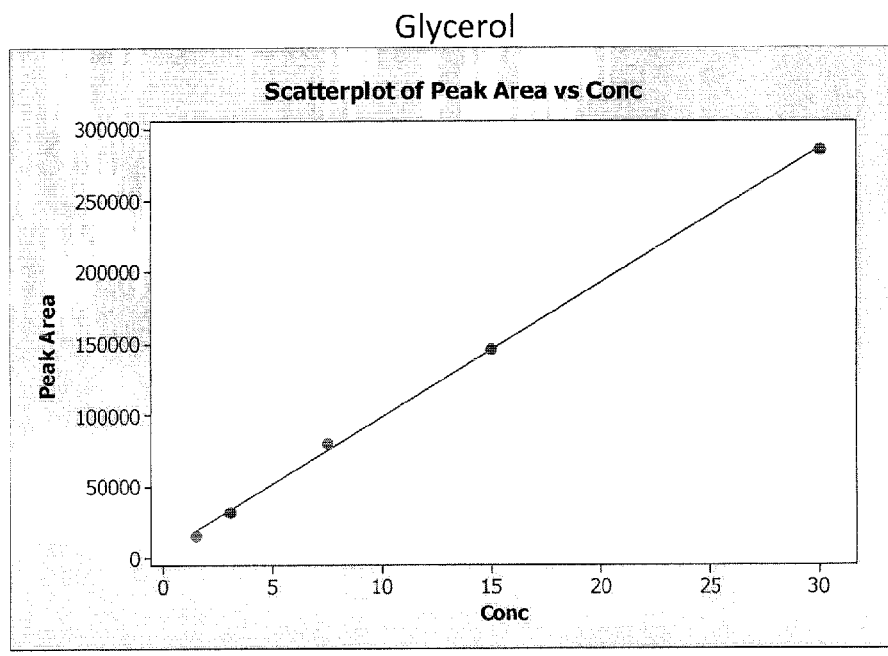
FIG. 4 is a scatterplot graph of glycerol consumption.
Figure 5:
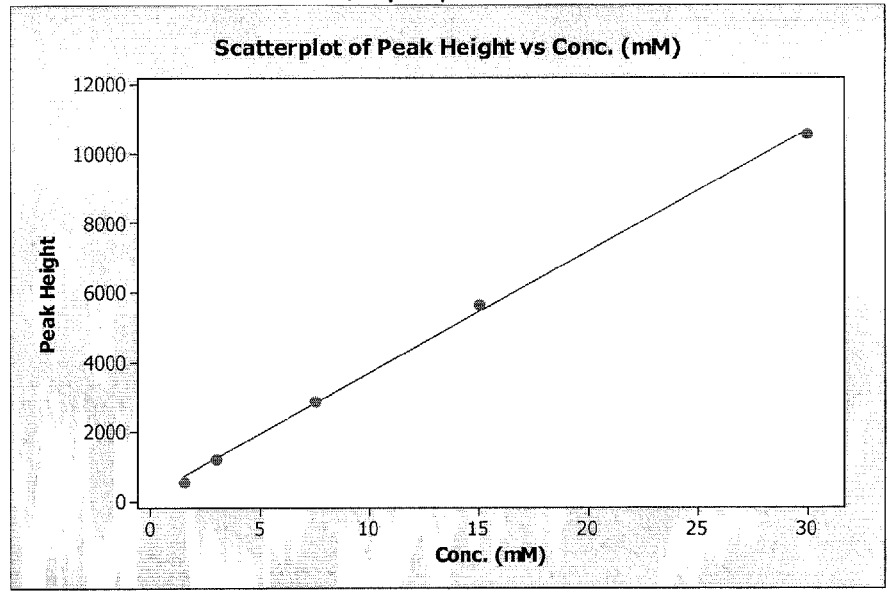
FIG. 5 is a scatterplot graph of 1,3-propanediol production.
Figure 6:
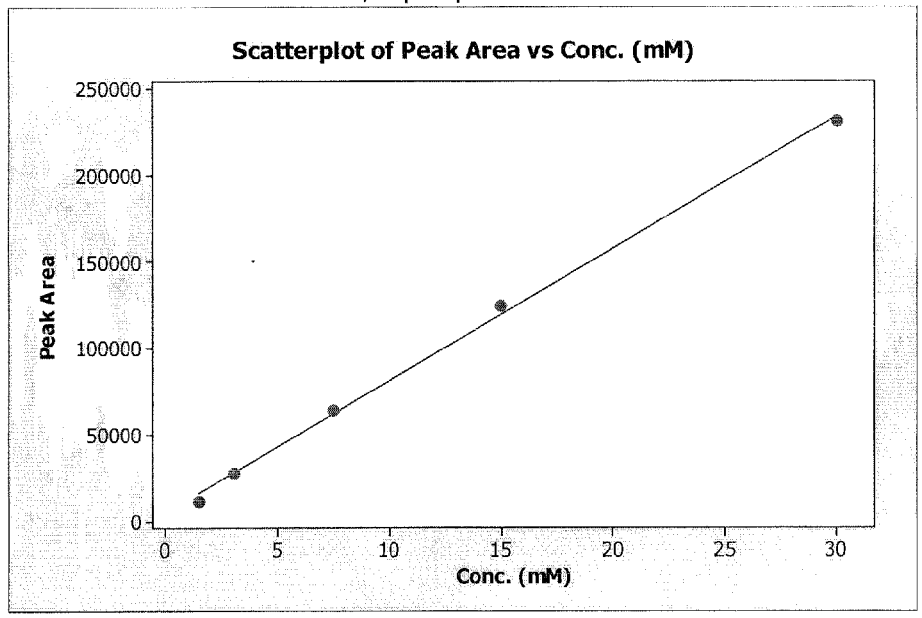
FIG. 6 is a scatterplot graph of 1,3-propanediol production.

*Halanaerobium hydrogeniformans* (formerly *Halanaerobium* strain *sapolanicus*) was isolated from haloalkaline (pH~10, 15- to 140-g/liter NaCl), anaerobic sediments of Soap Lake, Wash., with extraordinarily high sulfide concentrations of up to 10 g/liter. It is an obligately anaerobic, Gram-negative, nonmotile, nonsporulating, elongated rod bacterium (FIG. 2). It can utilize a range of $C_5$ and $C_6$ sugars with optimal growth at pH 11, 7% (wt/vol) NaCl, and 33° C., producing acetate, formate, and hydrogen as major metabolic end products. The genome sequence for *H. hydrogeniformans* was determined to improve assessment of its metabolic and bioenergy potential, particularly toward improving alkaline or haloalkaline pretreatment regimens for robust hydrogen production by this bacterium. The *H. hydrogeniformans* genome sequence was determined through a combination of Illumina (Bennett, S. 2004. Solexa, Ltd. Pharmacogenomics 5:433-438) and 454 (Margulies, M., et al. 2005. Genome sequencing in microfabricated high density picoliter reactors. Nature 437:376-380.) technologies. The Joint Genome Institute constructed and sequenced an Illumina GAii shotgun library which generated 27,639,916 reads totaling 2,100 Mb, a 454 Titanium standard library generated from 77,351 reads, and a paired-end 454 library with an average insert size of 10.607±2.651 kb that generated 160,293 reads totaling 82.3 Mb of 454 data. A total of 486 additional reactions and 6 shatter libraries were necessary to close gaps and to raise the finished sequence quality. Methods for determining the genome sequence were previously described (Elkins, J. G., et al. 2010. Complete genome sequence of the cellulolytic thermophile *Caldicellulosiruptor obsidiansis* OB47T. J. Bacteriol. doi:10.1128/JB.00950-10), and this is a "finished" genome (Chain, P. S. G., et al. 2009. Genome project standards in a new era of sequencing. Science 326:236-237). The total genome size was 2,613,116 bp, with final assembly based on 52.2 Mb of 454 draft data providing an average 21.5X genome coverage and 463 Mb of Illumina draft data providing an average 178X genome coverage. The genome is 33.1% G+C and contains 2,295 candidate protein-encoding gene models. The genome contains four separate rRNA operons, each containing a 5S, a 16S (SEQ ID NO:1), and a 23S rRNA gene, with 99.9 to 100% identity between 16S rRNA genes. The closest significant 16S rRNA gene matches (GenBank accession number GQ215697) were to other *Halanaerobium* species. However, all comparative species are physiologically different as they are neutrophilic. This whole-genome shotgun project has been deposited at DDBJ/EMBL/GenBank under the accession number CP002304.

Example 2

Production of 1,3-propanediol from Glycerol

The culture medium included (per liter): 70 g NaCl, 40 g $Na_2CO_3$, 6.3 g $K_2HPO_4$, 1 g yeast extract, 0.75 g $Na_2S$ (as a reductant), 0.6 g cysteine (as a reductant), along with 10 ml of basal medium stock solution and 10 ml of trace mineral solution. The basal medium stock solution included (per liter): 50 mg $NH_4NO_3$, 8.5 mg $MgCl_2.6H_2O$, 7.5 mg $SiO_2$, 4.5 mg $MnSO_4.H_2O$, 4.2 mg $CaCl_2.2H_2O$, 4 mg methylene blue (as an oxygen indicator), and 1.8 mg $FeSO_4.7H_2O$. The trace mineral solution included (per liter): 3 g $MgSO_4.7H_2O$, 1.63 g $Na_3$-NTA, 1 g NaCl, 0.64 g $MnCl_2.4H_2O$, 0.13 g $ZnCl_2$, 0.1 g $FeSO_4.7H_2O$, 0.1 g $CaCl_2.2H_2O$, 0.1 g $CoCl_2.6H_2O$, 0.03 g $NiSO_4.6H_2O$, 0.025 g $Na_2MoO_4.2H_2O$, 0.025 g $Na_2WO_4.2H_2O$, 0.01 g $AlK(SO_4)_2.12H_2O$, 0.01 g $H_3BO_3$, and 7 mg $CuCl_2.2H_2O$.

The culture bottles were prepared with 50 mL of culture medium and then amended with 2.5 mL of 600 mM Glycerol stock solution (to a final concentration of ~25 mM glycerol). Culture bottles were also amended with 2.5 mL of a 128 µg/mL Vitamin $B_{12}$ solution (to a final concentration of 53.33 µg/L). The headspace gas was exchanged to contain 100% $N_2$. The samples were incubated at 30° C. in a shaking incubator at 150 rpm for seven days. The results are shown in Table 1 below, from cultures that were amended with glycerol. Three replicates were amended with glycerol and bacteria. One culture amended with glycerol was not inoculated with the bacterium. Three additional replicates were amended with glycerol and vitamin $B_{12}$. One culture amended with glycerol and vitamin $B_{12}$ was not inoculated with the bacterium. These results clearly demonstrate that the bacterium consumed the glycerol amendments. Those cultures that also were amended with vitamin $B_{12}$ were able to consume a greater amount of glycerol than those that were not amended with this vitamin.

TABLE 1

| | Treatment | Day 0 Concentration of Glycerol (mM) | Day 7 Concentration of Glycerol (mM) |
|---|---|---|---|
| Replicate #1 | Glycerol | 26.706 | 8.047 |
| Replicate #2 | Glycerol | 26.565 | 7.603 |
| Replicate #3 | Glycerol | 26.446 | 7.939 |
| Without bacteria | Glycerol | 27.552 | 27.631 |
| Replicate #1 | Glycerol + $B_{12}$ | 25.458 | 0.870 |
| Replicate #2 | Glycerol + $B_{12}$ | 25.264 | 1.170 |
| Replicate #3 | Glycerol + $B_{12}$ | 25.484 | 1.118 |
| Without bacteria | Glycerol + $B_{12}$ | 26.331 | 26.546 |

Table 2 shows the results from cultures that were amended with glycerol. Three replicates were amended with glycerol and bacteria. One culture amended with glycerol was not inoculated with the bacterium. Three additional replicates were amended with glycerol and vitamin $B_{12}$. One culture amended with glycerol and vitamin $B_{12}$ was not inoculated with the bacterium. These results clearly demonstrate that the bacterium is capable of producing 1,3-propanediol. Those cultures that also were amended with vitamin $B_{12}$ were able to produce a greater amount of 1,3-propanediol than those that were not amended with this vitamin.

TABLE 2

| | Treatment | Day 0 Concentration of 1,3-propanediol (mM) | Day 7 Concentration of 1,3-propanediol (mM) |
|---|---|---|---|
| Replicate #1 | Glycerol | Not detected | 1.172 |
| Replicate #2 | Glycerol | Not detected | 1.104 |
| Replicate #3 | Glycerol | Not detected | 1.203 |
| Without bacteria | Glycerol | Not detected | Not detected |
| Replicate #1 | Glycerol + $B_{12}$ | Not detected | 11.947 |
| Replicate #2 | Glycerol + $B_{12}$ | Not detected | 11.619 |
| Replicate #3 | Glycerol + $B_{12}$ | Not detected | 11.786 |
| Without bacteria | Glycerol + $B_{12}$ | Not detected | Not detected |

Discussion

Standard Curves are shown in FIGS. 3-6. The differences between day 0 and day 7 glycerol and glycerol+$B_{12}$ treatment groups were analyzed. Glycerol consumption and 1,3-propanediol production were examined. Acetate production was also examined to determine the activity of the glycerol kinase pathway compared to the glycerol dehydratase pathway. Without protein analysis an exact measure of growth was not available, but acetate production can indicate at the very least that fermentation occurred and an estimate of how much glycerol is being utilized for pyruvate metabolism instead of 1,3-propanediol production.

Figure 7:
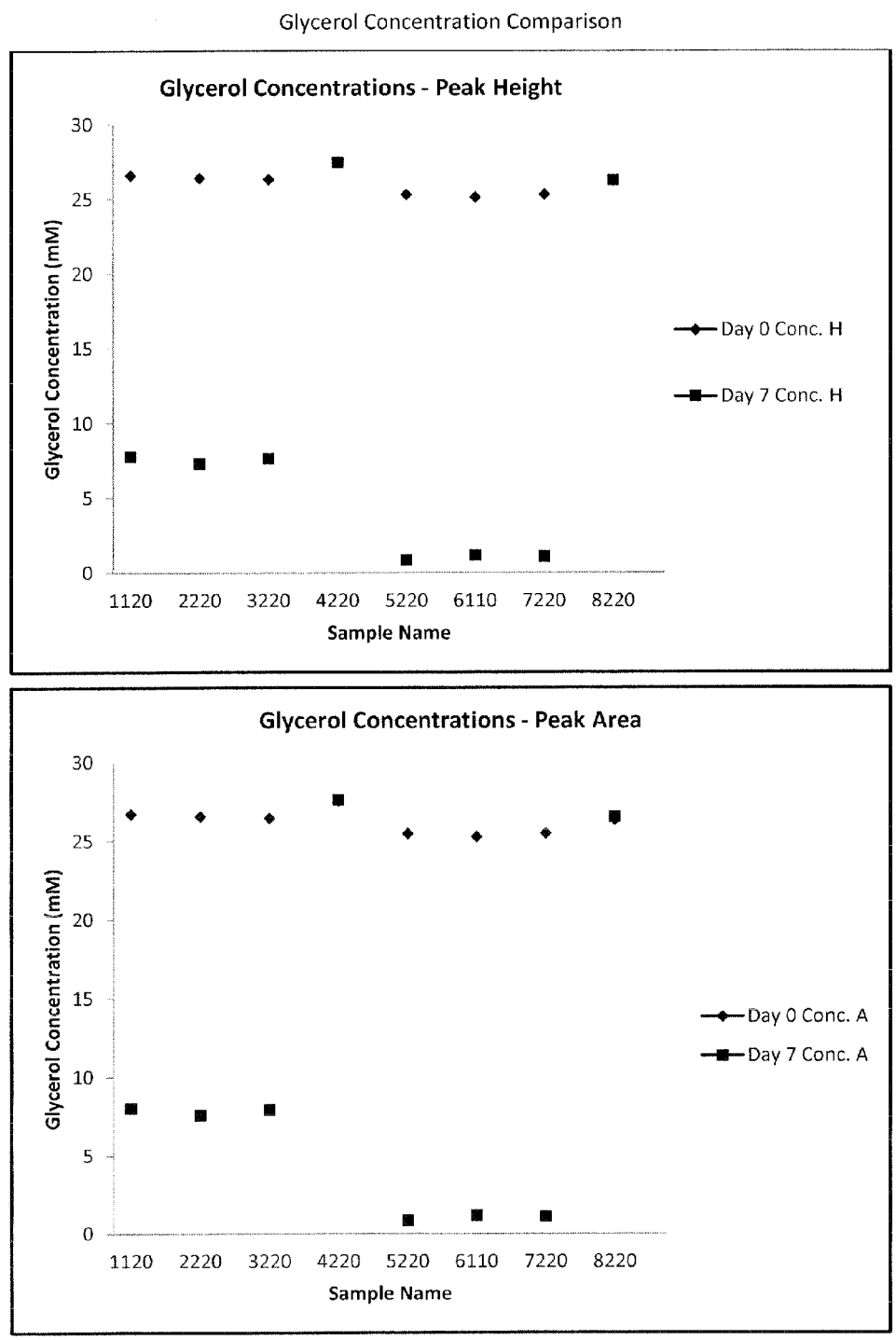
FIG. 7 shows scatterplot graphs showing glycerol concentration comparison between the Peek Height and the Peek Area.

The scatterplots in FIG. 7 shows that the cultures started with approximately the same concentration of glycerol, however after 7 days the cultures that were supplemented with $B_{12}$ (right hand side, 5-8000) utilized more of the total glycerol.

Figure 8:
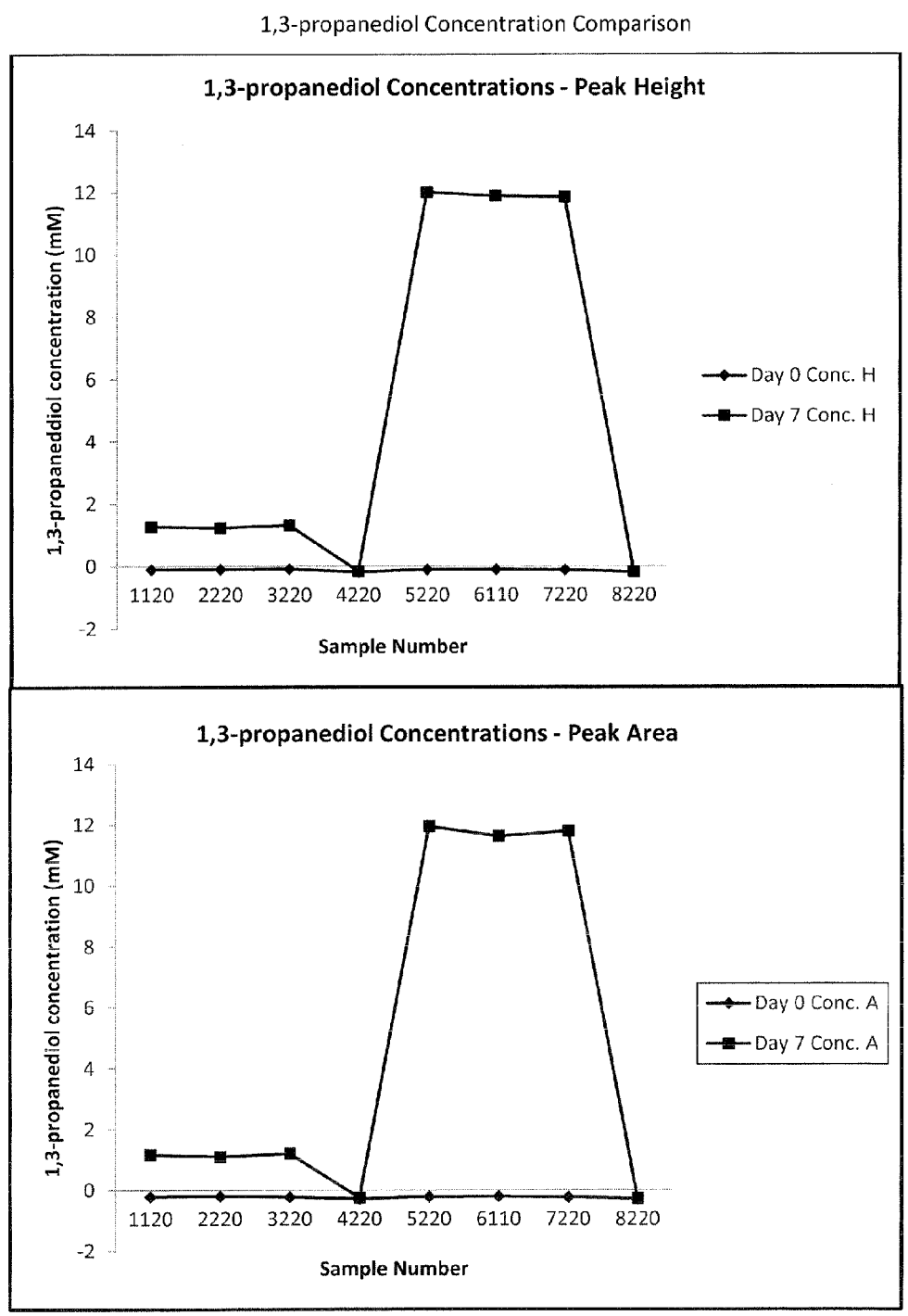
FIG. 8 shows scatterplot graphs showing 1,3-propanediol concentration comparison between the Peek Height and the Peek Area.

The scatterplots in FIG. 8 show that 1,3-propanediol production from the bacterium was observed under extreme conditions and increased production when $B_{12}$ is supplemented to the organism. With respect to acetate to examine "growth" roughly along with the activity of normal metabolism, both Peak Area and Peak Height in the $B_{12}$ supplemented cultures are about half of what is in just glycerol cultures which may help explain the decreased growth. A quick paired T test was performed to make sure the concentration differences were significant in both the Glycerol and Glycerol+$B_{12}$ cultures. Both p-values were <0.001 indicating a statistically significant production of 1,3-propanediol.

The final glycerol concentrations in the bottles at Day 0 was about 25.3 mM and we were producing about 12 mM 1,3-propanediol, resulting in about a 0.47 mol to mol ratio, however the $B_{12}$ supplementation was <64 µg/mL due to dilutions from inoculum and carbon source addition.

Example 3

Requirement of $B_{12}$

Anaerobic cultures were prepared in 160 mL serum bottles. The medium was prepared by boiling to degas under a $N_2$ blanket. As the medium cooled, reductant stock mix was added to the media that contained 0.75 g $Na_2S$ and 0.6 g cysteine per liter. Once the media was cooled, the flasks were transferred into a Coy anaerobic glove bag where the 50 mL of media was dispensed into 160 mL serum bottles filled and autoclaved (121° C., 20 min). After autoclaving, the headspace gas was exchanged for 80% $N_2$/20% $CO_2$ mixture. The bottles then were inoculated with a 10% inoculum from previous stock cultures. 30 mM glycerol was added. Vitamin $B_{12}$ supplementation from anaerobic, filter-sterilized stocks were added right before inoculation at 0 µg/L, 25 µg/L, 50 µg/L, 75 µg/L, and 100 µg/L.

Samples were taken every 24 hours. 5 mL syringes were degassed with $N_2$/$CO_2$ mix, and 1 mL of culture sample was removed for each of the sample periods. The sample was placed in a 1.5 mL Eppendorf tube, and centrifuged for 5 min at 13,000×g. The supernatant was decanted into another 1.5 mL Eppendorf tube, and frozen for HPLC analysis.

For HPLC analysis, filter sterilized samples (0.45 µM PTFE filters) were injected onto a 300×7.8 mm Aminex HPX-87H column (BioRad, Hercules, Calif.) maintained at 50° C. The mobile phase was 2.5 mM H2SO4 maintained at a constant flow rate of 0.6 ml/min and at approximately 2.2 MPa. Detection was done with both a UV 231 (at 210 nm) and refractive index monitor.

Figure 9:
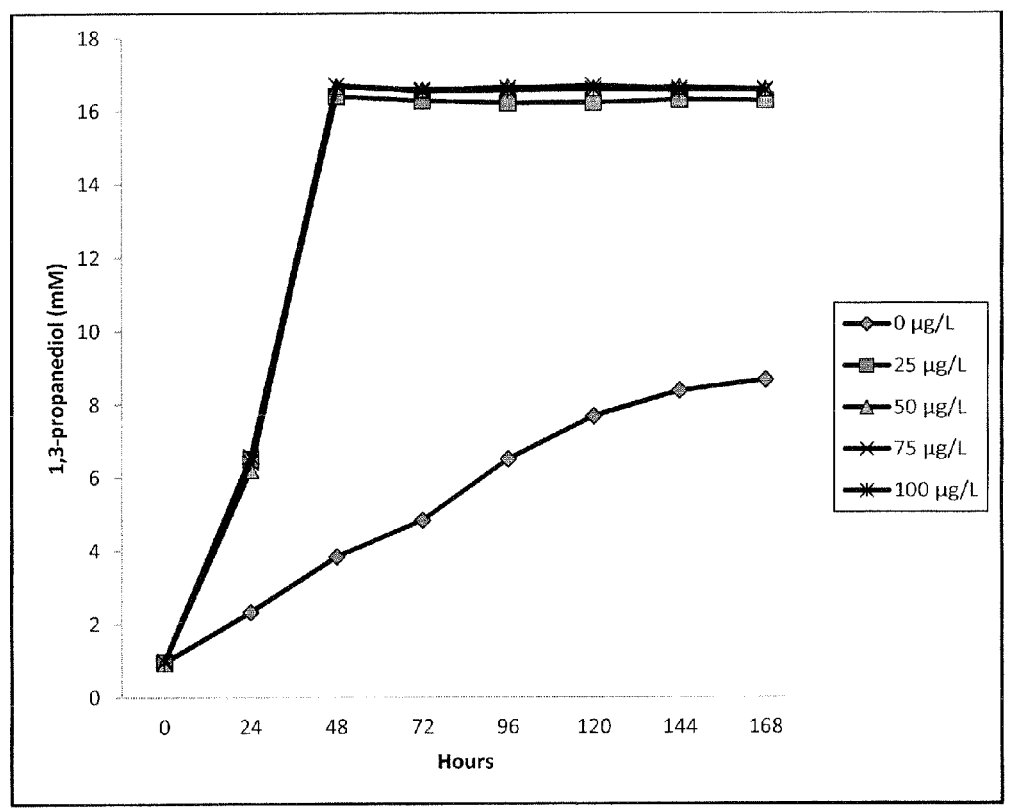
FIG. 9 is a graph showing the effect of increasing concentrations of vitamin Bit on 1,3-propanediol production (conversion).

Results Obtained:

The production capabilities of *H. hydrogeniformans* and the influence of vitamin $B_{12}$ supplementation were studied. A gradient was prepared to examine the maximum production of 1,3-propanediol from media containing 30 mM glycerol. Approximately 16.5 mM 1,3-propanediol was produced when the culture was amended with 25, 50, 75, or 100 µg/L vitamin $B_{12}$ and approximately 8.5 mM 1,3-propanediol when no vitamin $B_{12}$ was provided (FIG. 9). Table 3 indicates the percent mole/mole conversion of glycerol to 1,3-propanediol in *H. hydrogeniformans* cultures when supplemented with vitamin $B_{12}$.

TABLE 3

Percent mole/mole conversion of glycerol to 1,3-propanediol in *H. hydrogeniformans* cultures supplemented with vitamin $B_{12}$.

| $B_{12}$ Amendment, µg/L | % mol 1,3-propandiol/mol glycerol |
| --- | --- |
| 0 | 31.5 |
| 25 | 59.1 |
| 50 | 60.3 |
| 75 | 60.1 |
| 100 | 60.2 |

Example 4

Tolerance of *H. hydrogeniformans* to Glycerol

The tolerance of *H. hydrogeniformans* to concentrations of glycerol was examined. Anaerobic cultures were prepared in 160 mL serum bottles. The medium was prepared by boiling to degas under a $N_2$ blanket. As the medium cooled, reductant stock mix was added to the media that contained 0.75 g $Na_2S$ and 0.6 g cysteine per liter. Once the media was cooled, the flasks were transferred into a Coy anaerobic glove bag where the 50 mL of media was dispensed into 160 mL serum bottles filled and autoclaved (121° C., 20 min). After autoclaving, the headspace gas was exchanged for 80% $N_2$/20% $CO_2$ mixture. The bottles then were inoculated with a 10% inoculum from previous stock cultures. Sterilized glycerol was added to the serum bottles to achieve 7.5, 15, 30, 60, 120, 240, 480, 960, and 1920 mM. Growth was examined by turbidity readings taken at 600 nM. It was determined that *H. hydrogeniformans* was capable of growth at 7.5, 15, 30, 60, 120, 240, 480, 960, and 1920 mM glycerol. It did not exhibit any growth when glycerol was not present in the medium. The data indicate that *H. hydrogeniformans* can tolerate at least 1M glycerol in addition to 7% (w/v) and pH 11.

TABLE 4

| | Glycerol Concentration (mM) | | | | | | | | | |
| --- | --- | --- | --- | --- | --- | --- | --- | --- | --- | --- |
| | 0 | 7.5 | 15 | 30 | 60 | 120 | 240 | 480 | 960 | 1920 |
| Growth | X | X | X | X | X | X | X | X | X | — |

Example 5

Tolerance of *H. hydrogeniformans* to 1,3-propanediol

The tolerance of *H. hydrogeniformans* to increasing concentrations of 1,3-propanediol was examined. Anaerobic cultures were prepared in 160 mL serum bottles. The medium was prepared by boiling to degas under a $N_2$ blanket. As the medium cooled, reductant stock mix was added to the media that contained 0.75 g $Na_2S$ and 0.6 g cysteine per liter. Once the media was cooled, the flasks were transferred into a Coy anaerobic glove bag where the 50 mL of media was dispensed into 160 mL serum bottles filled and autoclaved (121° C., 20 min). After autoclaving, the headspace gas was exchanged for 80% $N_2$/20% $CO_2$ mixture. The bottles then were inoculated with a 10% inoculum from previous stock cultures and amended with 30 mM glycerol. Sterilized 1,3-propanediol was added to the serum bottles to achieve 10, 30, 60, 120, 380, and 750 mM. Growth was examined by turbidity readings taken at 600 nM. It was determined that *H. hydrogeniformans* was capable of growth when 0, 10, 30, 60, 120, and 380 mM 1,3-propanediol concentrations were present. The data indicates that *H. hydrogeniformans* can tolerate at least 0.38M 1,3-propanediol in addition to 7% (w/v) and pH 11.

TABLE 5

| 1,3-propanediol Concentration (mM) | | | | | | |
|---|---|---|---|---|---|---|
| 0 | 10 | 30 | 60 | 120 | 380 | 750 |
| Growth X | X | X | X | X | X | — |

Example 6

Tolerance of *H. hydrogeniformans* to Crude Glycerol

The tolerance of *H. hydrogeniformans* to crude glycerol was examined. Anaerobic cultures were prepared in 160 mL serum bottles. The medium was prepared by boiling to degas under a $N_2$ blanket. As the medium cooled, reductant stock mix was added to the media that contained 0.75 g $Na_2S$ and 0.6 g cysteine per liter. Once the media was cooled, the flasks were transferred into a Coy anaerobic glove bag where the 50 mL of media was dispensed into 160 mL serum bottles filled and autoclaved (121° C., 20 min). After autoclaving, the headspace gas was exchanged for 80% $N_2$/20% $CO_2$ mixture. The bottles then were inoculated with a 10% inoculum from previous stock cultures. Crude glycerol, obtained from a small biodiesel producer, was added at 0.1% and 0.5% concentrations. No purification steps were applied to the crude glycerol. Growth, after one week, was examined by turbidity readings taken at 600 nM. It was determined that *H. hydrogeniformans* was capable of growth when exposed to crude, unpurified glycerol. *H. hydrogeniformans* can grow in at least 0.5% crude glycerol. Slow growth in 0.1% crude, most likely due to low glycerol concentration. Even slower growth in 0.5% crude glycerol.

DISCUSSION

The work has identified 1,3-propanediol production capability at pH 11 and 7% (w/v) NaCl of *H. hydrogeniformans*. The microorganism is capable of growth in 1M glycerol (along with 7% NaCl and a pH of 11) and 380 mM of 1,3-propanediol. In the absence of $B_{12}$, the conversion rate is 31%. With $B_{12}$ supplementation (>25 μg/L $B_{12}$), the conversion rate is approximately 60% conversion. The microorganism is also capable of growing in at least 0.5% crude glycerol, without treatment.

What is claimed:

1. A method of producing 1,3-propanediol, said method comprising fermenting *Halanaerobium hydrogeniformans* with a source of glycerol in a fermentation reactor, whereby 1,3-propanediol is produced, said reactor comprising an inlet for said source of glycerol, a fermentation chamber containing said *H. hydrogeniformans* in culture media, and an outlet for removing said 1,3-propanediol.

2. The method of claim 1, further comprising recovering said 1,3-propanediol.

3. The method of claim 1, wherein said source of glycerol is chemical waste from biodiesel production comprising glycerol.

4. The method of claim 3, wherein said chemical waste comprises crude glycerol.

5. The method of claim 3, wherein said fermenting is carried out without neutralization of said chemical waste pH prior to said fermenting.

6. The method of claim 3, wherein said fermenting is carried out without diluting the salinity of said chemical waste prior to said fermenting.

7. The method of claim 3, said chemical waste further comprising methanol, wherein said fermenting is carried out without removing said methanol from said chemical waste prior to said fermenting.

8. The method of claim 1, wherein said fermenting comprises culturing said *H. hydrogeniformans* with said source of glycerol in a culture medium to yield a fermentation culture.

9. The method of claim 8, wherein said culture medium comprises Vitamin $B_{12}$.

10. The method of claim 8, wherein said fermentation culture has a salt content of greater than or equal to 5% w/v.

11. The method of claim 1, wherein said fermenting is carried out at a pH of greater than or equal to 10.

12. The method of claim 1, said fermenting is carried out under substantially anaerobic conditions.

13. The method of claim 1, wherein said *H. hydrogeniformans* is the organism deposited as ATCC designation No. PTA-10410.

14. The method of claim 1, wherein said *H. hydrogeniformans* comprises an endogenous gene coding for a glycerol dehydratase or an enzyme having glycerol dehydratase activity.

15. The method of claim 14, wherein said gene comprises a DNA sequence comprising SEQ ID NO:2 or a sequence having at least 98% sequence identity with SEQ ID NO: 2.

16. The method of claim 14, wherein said glycerol dehydratase comprises SEQ ID NO:3, or a sequence having at least 98% sequence identity with SEQ ID NO: 3.

17. The method of claim 1, wherein said *H. hydrogeniformans* comprises an endogenous gene coding for an iron-containing alcohol dehydrogenase or an enzyme having alcohol dehydrogenase activity.

18. The method of claim 17, wherein said gene comprises a DNA sequence comprising SEQ ID NO:4 or 6, or a sequence having at least 98% sequence identity with SEQ ID NO: 4 or 6.

19. The method of claim 17, wherein said iron-containing alcohol dehydrogenase comprises SEQ ID NO:5 or 7, or a sequence having at least 98% sequence identity with SEQ ID NO: 5 or 7.

20. A method of producing 1,3-propanediol, said method comprising fermenting *Halanaerobium hydrogeniformans* with a source of glycerol, whereby 1,3-propanediol is produced, wherein said source of glycerol is chemical waste from biodiesel production comprising glycerol and methanol, wherein said fermenting is carried out without removing said methanol from said chemical waste prior to said fermenting.

* * * * *

SEQUENCE LISTING

```
<160> NUMBER OF SEQ ID NOS: 7

<210> SEQ ID NO 1
<211> LENGTH: 1191
<212> TYPE: DNA
<213> ORGANISM: Halanaerobium hydrogenoformans
<220> FEATURE:
<221> NAME/KEY: gene
<222> LOCATION: (1)..(1191)
<223> OTHER INFORMATION: 16S rRNA
<220> FEATURE:
<221> NAME/KEY: misc_feature
<222> LOCATION: (621)..(621)
<223> OTHER INFORMATION: n is a, c, g, or t

<400> SEQUENCE: 1
ggaagccttc gggcggaaga cgagactaga tagtggcgga cgggtgagta acacgtggat      60
aacctgtcct caagtctggg ataacctggc gaaagtcggg ctaatcccgg gtaagctgag     120
agtgtggcat cacacaatca gaaaaggtgc tattagcatc gtttgaggag gggtccgcgg     180
tagattagct agctggtgag gtaatggctc accagggcga caatctatag ctggtctgag     240
aggacgatca gtcacactgg aactgagaca cggtccagac tcctacggga ggcagcagtg     300
gggaatcttc cacaatgggc gaaagcctga tggagcaacg ccgcgtgagt gaagaaggtc     360
ttaggattgt aaagctctgt ccttagggaa gaaccgtggg tatagaaaat gatacccacc     420
tgacggtacc tttggaggaa gcactggcta actacgtgcc agcagccgcg gtaatacgta     480
gagtgcaagc gttgtccgga attattgggc gtaaagggta cgcaggcgga taatcaagtc     540
aagcgtgaaa ggtgtcggct taaccgacag actgcgtttg aaactggtta tcttgagtgt     600
aacagaggag agtggaattc ntagtgtagt ggtgaaatac gtagatatta ggaagaacac     660
cagtggcgaa ggcgactctc tggttaaca ctgacgctga ggtacgaaag ctgggggagc      720
gaacgggatt agatacccccg gtagtcccag ccgtaaacga tggatactag gtgttggagg     780
ttcgaatcct tcagtgccgg agttaacgca ttaagtatcc cgcctgggga ttacgatcgc     840
aagattgaaa ctcaaaggaa ttgacggggg cccgcacaag cggtggagca tgtggtttaa     900
```

```
ttcgaagcaa cgcgaagaac cttaccgaga attgacatcc cgtgactacc tgtgaaagca      960
gggtttggca tttatgtcac acggagacag gtggtgcatg gctgtcgtca gctcgtgtcg     1020
tgagatgttg ggttaagtcc cgcaacgagc gcaacccctg ttcttagttg ccagcgagta     1080
atgtcgggga ctctaagaag actgccggtg aaagtcggag gaaggtgggg atgacgtcaa     1140
gtcctcatgc cctttatatc tcgggctaca cacgtgctac aatggttggt a              1191
```

<210> SEQ ID NO 2
<211> LENGTH: 1671
<212> TYPE: DNA
<213> ORGANISM: Halanaerobium hydrogenoformans
<220> FEATURE:
<221> NAME/KEY: gene
<222> LOCATION: (1)..(1671)
<223> OTHER INFORMATION: glycerol dehydratase (+)strand

<400> SEQUENCE: 2

```
gtgaaaaggt ccaagcgatt tttagaactt gaaaaaaggc cgattagtaa tgatggattt       60
atcaatgaat ggccagaagc tggtcttgtg gctatggaag gacccaatga tccaaaacca      120
agcgttagag ttgaaaatgg taaaatagta gagttagatg gtaaaagaag agaagaattt      180
gacatgttag actctttat tgccgatcat actcttgatc tagatatagt tgaagatgtt      240
atggcccagg attcaaaaga actggctcat aaaatagtag acataaatgt ttgtagagat      300
gaggttaaga gatttggttt aggtatgacc cctgctaaag ttgttgaagt ggttggtcat      360
atgaatgttg ttgaaatgat gatggcggtt cagaagatga gagctagaaa aactccttct      420
aaccagtgcc atgttacaaa tgtaaaagac cacccagcat tattagctgc agatgcagca      480
gaagcagctc tgcgtggttt tgatgaaatg gaaacaacag taggtatagt tagatatgcg      540
ccttctaacg ctatttcaat catggtaggt tcacaaactg gccgtggtgg agttttaacc      600
cagtgtgctg ttgaggaagc tatgaattta gaaatgggta tgcgtggatt tacagcctat      660
gctgaaacag tttcagtata tggtacagag caggtatttg ttgatggtga tgatacacca      720
tggtctaaga gtttcttagc atctgcttat gcatcccgtg gattaaaaat gagatatact      780
tctggtaccg gttctgaagc agaaatggga tttgctgatg gtaaatctat gctttatctt      840
gaagctcgct gcttatatat gaccaaaggt gcaggagttc agggtataca gaatggttca      900
atcagttgta ttggtgtgcc cggggcagtt ccatccggag ttagagcaat tctggctgaa      960
aacttaattg ccatgttact tgacttagag tgtgcatctg gtaatgatca gacatttact     1020
cactcaagta caagaagaac tgctagaatg ttaatgcagt ttttgcctgg tactgacttt     1080
gtattctcag gttacagtgc tgtaccaaac tatgataaca tgtttgcagg ttcaactcat     1140
gatgttgatg actatgatga ctatctaaca ttacagcgtg acttaaaagt taatggtgga     1200
ttagtacctg tagatgaaga agatgttatt aaagttagaa acaaaggtgt tagagcttta     1260
caggcagtat ttaaagaaat cggtatgcct gatattacag atgaagaagt agaggctgca     1320
acatatgccc acggtagtaa agatatgcct gaccgtgatg taagagaaga tttcagaggt     1380
atagaagaaa tgctcaataa aggaaccaca ggtgttcaaa tcgtacaggc acttgctaaa     1440
catggatttg aagatgtagc tgaaaacttc tttaatctct aaaacagag aattgctgga     1500 gattatctcc atacatcagc gatctttgat gaaaacttcc atgcaataag tgctgttaat     1560
gataaaaatg attatgcagg tcctggaaca ggatatagag tttctgatga actctgggaa     1620
aaacttaaaa atgttagatt cgctaaagat attgacgaaa taggagaata a              1671
```

```
<210> SEQ ID NO 3
<211> LENGTH: 556
<212> TYPE: PRT
<213> ORGANISM: Halanaerobium hydrogenoformans
<220> FEATURE:
<221> NAME/KEY: MISC_FEATURE
<222> LOCATION: (1)..(556)
<223> OTHER INFORMATION: glycerol dehydratase

<400> SEQUENCE: 3
```

Met Lys Arg Ser Lys Arg Phe Leu Glu Leu Glu Lys Arg Pro Ile Ser
1               5                   10                  15

Asn Asp Gly Phe Ile Asn Glu Trp Pro Glu Ala Gly Leu Val Ala Met
            20                  25                  30

Glu Gly Pro Asn Asp Pro Lys Pro Ser Val Arg Val Glu Asn Gly Lys
        35                  40                  45

Ile Val Glu Leu Asp Gly Lys Arg Glu Glu Phe Asp Met Leu Asp
    50                  55                  60

Ser Phe Ile Ala Asp His Thr Leu Asp Leu Asp Ile Val Glu Asp Val
65                  70                  75                  80

Met Ala Gln Asp Ser Lys Glu Leu Ala His Lys Ile Val Asp Ile Asn
                85                  90                  95

Val Cys Arg Asp Glu Val Lys Arg Phe Gly Leu Gly Met Thr Pro Ala
            100                 105                 110

Lys Val Val Glu Val Val Gly His Met Asn Val Val Glu Met Met Met
        115                 120                 125

Ala Val Gln Lys Met Arg Ala Arg Lys Thr Pro Ser Asn Gln Cys His
    130                 135                 140

Val Thr Asn Val Lys Asp His Pro Ala Leu Leu Ala Ala Asp Ala Ala
145                 150                 155                 160

Glu Ala Ala Leu Arg Gly Phe Asp Glu Met Glu Thr Thr Val Gly Ile
                165                 170                 175

Val Arg Tyr Ala Pro Ser Asn Ala Ile Ser Ile Met Val Gly Ser Gln
            180                 185                 190

Thr Gly Arg Gly Gly Val Leu Thr Gln Cys Ala Val Glu Glu Ala Met
        195                 200                 205

Glu Leu Glu Met Gly Met Arg Gly Phe Thr Ala Tyr Ala Glu Thr Val
    210                 215                 220

Ser Val Tyr Gly Thr Glu Gln Val Phe Val Asp Gly Asp Asp Thr Pro
225                 230                 235                 240

Trp Ser Lys Ser Phe Leu Ala Ser Ala Tyr Ala Ser Arg Gly Leu Lys
                245                 250                 255

Met Arg Tyr Thr Ser Gly Thr Gly Ser Glu Ala Glu Met Gly Phe Ala
            260                 265                 270

Asp Gly Lys Ser Met Leu Tyr Leu Glu Ala Arg Cys Leu Tyr Met Thr
        275                 280                 285

Lys Gly Ala Gly Val Gln Gly Ile Gln Asn Gly Ser Ile Ser Cys Ile
    290                 295                 300

Gly Val Pro Gly Ala Val Pro Ser Gly Val Arg Ala Ile Leu Ala Glu
305                 310                 315                 320

Asn Leu Ile Ala Met Leu Leu Asp Leu Glu Cys Ala Ser Gly Asn Asp
                325                 330                 335

Gln Thr Phe Thr His Ser Ser Thr Arg Arg Thr Ala Arg Met Leu Met
            340                 345                 350

Gln Phe Leu Pro Gly Thr Asp Phe Val Phe Ser Gly Tyr Ser Ala Val

```
                     355                 360                 365
Pro Asn Tyr Asp Asn Met Phe Ala Gly Ser Thr His Asp Val Asp
        370                 375                 380
Tyr Asp Asp Tyr Leu Thr Leu Gln Arg Asp Leu Lys Val Asn Gly Gly
385                 390                 395                 400
Leu Val Pro Val Asp Glu Glu Asp Val Ile Lys Val Arg Asn Lys Gly
                405                 410                 415
Val Arg Ala Leu Gln Ala Val Phe Lys Glu Ile Gly Met Pro Asp Ile
            420                 425                 430
Thr Asp Glu Glu Val Glu Ala Ala Thr Tyr Ala His Gly Ser Lys Asp
        435                 440                 445
Met Pro Asp Arg Asp Val Arg Glu Asp Phe Arg Gly Ile Glu Glu Met
    450                 455                 460
Leu Asn Lys Gly Thr Thr Gly Val Gln Ile Val Gln Ala Leu Ala Lys
465                 470                 475                 480
His Gly Phe Glu Asp Val Ala Glu Asn Phe Phe Asn Leu Leu Lys Gln
                485                 490                 495
Arg Ile Ala Gly Asp Tyr Leu His Thr Ser Ala Ile Phe Asp Glu Asn
            500                 505                 510
Phe His Ala Ile Ser Ala Val Asn Asp Lys Asn Asp Tyr Ala Gly Pro
        515                 520                 525
Gly Thr Gly Tyr Arg Val Ser Asp Glu Leu Trp Glu Lys Leu Lys Asn
    530                 535                 540
Val Arg Phe Ala Lys Asp Ile Asp Glu Ile Gly Glu
545                 550                 555

<210> SEQ ID NO 4
<211> LENGTH: 1167
<212> TYPE: DNA
<213> ORGANISM: Halanaerobium hydrogenoformans
<220> FEATURE:
<221> NAME/KEY: misc_feature
<222> LOCATION: (1)..(1167)
<223> OTHER INFORMATION: iron-containing alcohol dehydrogenase (+)strand

<400> SEQUENCE: 4
atgtatgatt atatgttacc aacagtaaat tttatgggag caggttctgt taaagtagta      60
ggagaaagag caaaaattct gggtgcaaaa aaagttcttt tagtcactga tgactttta     120 agtaatctag atggtggacc cttttgagacc gtagttaaat atattgaaga agcgggttta    180
gcatatgctg tttatgatgg tgtaaaggct aatcccagag atactaatgt ttatgaaggc    240
ttagaaattt acgaaaatga aaattgtgat atgataatta cagtaggtgg aggaagtcct    300
catgattgtg gtaaggcaat cggggttgct gcaactcatg atggagattt atataaggat    360
tatgccggag tagaaaaatt agaaaatgaa acacctgcta tgatctgtgt taatacaact    420
gctggaacag ccagtgaggt taccagacat gcagtaataa ctgatacttc tcaaacacct    480
catgtaaagt ttgtaattgt cagctggcgt aatgtgccag atgtgtctat taatgatccg    540
gaactaatgg tagctaaacc tgctgcatta actgcagcta caggaatgga tgctttaact    600
catgctttag aaacctttgt ttcaacaggt gctaattcat taacagatgc agctgccaaa    660
gaagctatgg aactaatagc taagtactta agaagggcag tttataatgg agaagatatt    720
gaagccagag aagagatggc taatgcttca gtttagccg gttttgcctt caacaatggt    780
ggtttaggtt atgttcatgc tatggcccat cagttgggtg gatttatga tatgccacat    840 gggatagcca atgcaatcct cctgcctta gttgaaaaat ttaatttagg agctaaaata    900
```

```
gataaatttg ccaaggtcgc agaaatattt ggagttccta cagctgggct ttctaaaaga     960
gaagctgctg aaaaatcttt agatgcaatt gtacagctgg ctgaagatat cggaatcccg    1020
acttctttaa gtgaatcaga atatgatgtc aaagaagaag attttgagga gatggcaaga   1080
ttagctttag aagatggtaa tgctttaagc aatcctagaa aagcaactca agcagaaatt   1140
gccggaatct ttaaagcagc ttattaa                                       1167
```

<210> SEQ ID NO 5
<211> LENGTH: 388
<212> TYPE: PRT
<213> ORGANISM: Halanaerobium hydrogenoformans
<220> FEATURE:
<221> NAME/KEY: MISC_FEATURE
<222> LOCATION: (1)..(388)
<223> OTHER INFORMATION: iron-containing alcohol dehydrogenase

<400> SEQUENCE: 5

```
Met Tyr Asp Tyr Met Leu Pro Thr Val Asn Phe Met Gly Ala Gly Ser
1               5                   10                  15

Val Lys Val Val Gly Glu Arg Ala Lys Ile Leu Gly Ala Lys Lys Val
            20                  25                  30

Leu Leu Val Thr Asp Asp Phe Leu Ser Asn Leu Asp Gly Gly Pro Phe
        35                  40                  45

Glu Thr Val Val Lys Tyr Ile Glu Glu Ala Gly Leu Ala Tyr Ala Val
    50                  55                  60

Tyr Asp Gly Val Lys Ala Asn Pro Arg Asp Thr Asn Val Tyr Glu Gly
65                  70                  75                  80

Leu Glu Ile Tyr Glu Asn Glu Asn Cys Asp Met Ile Ile Thr Val Gly
                85                  90                  95

Gly Gly Ser Pro His Asp Cys Gly Lys Ala Ile Gly Val Ala Ala Thr
            100                 105                 110

His Asp Gly Asp Leu Tyr Lys Asp Tyr Ala Gly Val Glu Lys Leu Glu
        115                 120                 125

Asn Glu Thr Pro Ala Met Ile Cys Val Asn Thr Thr Ala Gly Thr Ala
    130                 135                 140

Ser Glu Val Thr Arg His Ala Val Ile Thr Asp Thr Ser Gln Thr Pro
145                 150                 155                 160

His Val Lys Phe Val Ile Val Ser Trp Arg Asn Val Pro Asp Val Ser
                165                 170                 175

Ile Asn Asp Pro Glu Leu Met Val Ala Lys Pro Ala Ala Leu Thr Ala
            180                 185                 190

Ala Thr Gly Met Asp Ala Leu Thr His Ala Leu Glu Thr Phe Val Ser
        195                 200                 205

Thr Gly Ala Asn Ser Leu Thr Asp Ala Ala Ala Lys Glu Ala Met Glu
    210                 215                 220

Leu Ile Ala Lys Tyr Leu Arg Arg Ala Val Tyr Asn Gly Glu Asp Ile
225                 230                 235                 240

Glu Ala Arg Glu Glu Met Ala Asn Ala Ser Val Leu Ala Gly Phe Ala
                245                 250                 255

Phe Asn Asn Gly Gly Leu Gly Tyr Val His Ala Met Ala His Gln Leu
            260                 265                 270

Gly Gly Phe Tyr Asp Met Pro His Gly Ile Ala Asn Ala Ile Leu Leu
        275                 280                 285

Pro Tyr Val Glu Lys Phe Asn Leu Gly Ala Lys Ile Asp Lys Phe Ala
    290                 295                 300
```

```
Lys Val Ala Glu Ile Phe Gly Val Pro Thr Ala Gly Leu Ser Lys Arg
305                 310                 315                 320

Glu Ala Ala Glu Lys Ser Leu Asp Ala Ile Val Gln Leu Ala Glu Asp
                325                 330                 335

Ile Gly Ile Pro Thr Ser Leu Ser Glu Ser Tyr Asp Val Lys Glu
            340                 345                 350

Glu Asp Phe Glu Glu Met Ala Arg Leu Ala Leu Glu Asp Gly Asn Ala
        355                 360                 365

Leu Ser Asn Pro Arg Lys Ala Thr Gln Ala Glu Ile Ala Gly Ile Phe
    370                 375                 380

Lys Ala Ala Tyr
385

<210> SEQ ID NO 6
<211> LENGTH: 1287
<212> TYPE: DNA
<213> ORGANISM: Halanaerobium hydrogenoformans
<220> FEATURE:
<221> NAME/KEY: misc_feature
<222> LOCATION: (1)..(1287)
<223> OTHER INFORMATION: iron-containing alcohol dehydrogenase (+)strand

<400> SEQUENCE: 6
atgtccgatt attatgatta tatgctgcca actgtaaatt ttatgggacc tggctgtgta      60
gaggttgttg gagaaaggtg caaaatttta ggtgcaaaaa aagttttaat agtgactgac     120 agcttttttaa gaaatatgga gggtggacct gtagatcagg ttgttaaata tttaaagaaa    180
gctaatttga attatgcatt ttatgatgaa gttgaaccta atcctaaaga tgtaaatgtt     240
tatgctgggc ttaagattta cgaaagagaa aattgtgaca tgattgtaac tattggtggt     300
ggaagtgctc atgattgtgg aaaagcaatt ggagttgcag ctacccatga tggtgattta     360
tacaaagatt atgcgggtat tgaaaaacta gaaaatgaaa ctcctcccat ggtctgtgta     420
aatacaaccg ctggaactgc tagtgaggtt accaggcaca cagttattac tgacacttct     480
cagactccaa acgttaaatt tgttatagta agttggagga atacaccgga tgtctctatc     540
aatgatccgg aacttatggt tggtaaacca cctggattaa ctgctgcaac cggtatggat     600
gctctgaccc atgcagtaga acatatgtc tcaactaatg caaatgcttt aactgatgca      660
gcagctatta atcaatcga attggtcgca ataatttaa gaaaagtcgt taaagatggt       720
caggatatta agcacgtga aaatatggct aatgcatccg tattatctgg tttcgccttc      780
aacaatggtg gcctgggtta tgttcatgct atggctcatc aactaggtgg tttttatgat     840
atgccacacg gtatagctaa tgccatttta ctgccttatg tagaaaagtt taatcttggc     900
acagatgtag agcgtttctc aaatattact gaaatatttg gcaaagaaca agtaaaata     960 tctaataatc cagaagctca agaatcaatt aaagctatta agatgaaat cgataagcta    1020 aaagattta aaaaaatcgc tgaagttttt ggtgttgata caagtaatat gtcaacaaga    1080
gaagcggctg aagcttcttt agacgccatt aaagaactag ctcgagatat tggaattcca    1140
agctctctga gcgaatctaa atttgatgtt aaaagagacg attttgaaga aatggcaaaa    1200
ttagctttag aggatggtaa tgctggaact aaccctagaa aaggtagtgt agaagatatt    1260
gtaagaatat ttgaagatgc ctttttaa                                      1287

<210> SEQ ID NO 7
<211> LENGTH: 428
<212> TYPE: PRT
```

<213> ORGANISM: Halanaerobium hydrogenoformans
<220> FEATURE:
<221> NAME/KEY: MISC_FEATURE
<222> LOCATION: (1)..(428)
<223> OTHER INFORMATION: iron-containing alcohol dehydrogenase

<400> SEQUENCE: 7

```
Met Ser Asp Tyr Tyr Asp Tyr Met Leu Pro Thr Val Asn Phe Met Gly
1               5                   10                  15

Pro Gly Cys Val Glu Val Val Gly Glu Arg Cys Lys Ile Leu Gly Ala
            20                  25                  30

Lys Lys Val Leu Ile Val Thr Asp Ser Phe Leu Arg Asn Met Glu Gly
                35                  40                  45

Gly Pro Val Asp Gln Val Val Lys Tyr Leu Lys Lys Ala Asn Leu Asn
        50                  55                  60

Tyr Ala Phe Tyr Asp Glu Val Glu Pro Asn Pro Lys Asp Val Asn Val
65                  70                  75                  80

Tyr Ala Gly Leu Lys Ile Tyr Glu Arg Glu Asn Cys Asp Met Ile Val
                85                  90                  95

Thr Ile Gly Gly Gly Ser Ala His Asp Cys Gly Lys Ala Ile Gly Val
            100                 105                 110

Ala Ala Thr His Asp Gly Asp Leu Tyr Lys Asp Tyr Ala Gly Ile Glu
            115                 120                 125

Lys Leu Glu Asn Glu Thr Pro Pro Met Val Cys Val Asn Thr Thr Ala
130                 135                 140

Gly Thr Ala Ser Glu Val Thr Arg His Thr Val Ile Thr Asp Thr Ser
145                 150                 155                 160

Gln Thr Pro Asn Val Lys Phe Val Ile Val Ser Trp Arg Asn Thr Pro
                165                 170                 175

Asp Val Ser Ile Asn Asp Pro Glu Leu Met Val Gly Lys Pro Pro Gly
            180                 185                 190

Leu Thr Ala Ala Thr Gly Met Asp Ala Leu Thr His Ala Val Glu Thr
        195                 200                 205

Tyr Val Ser Thr Asn Ala Asn Ala Leu Thr Asp Ala Ala Ala Ile Lys
210                 215                 220

Ser Ile Glu Leu Val Ala Asn Asn Leu Arg Lys Val Val Lys Asp Gly
225                 230                 235                 240

Gln Asp Ile Lys Ala Arg Glu Asn Met Ala Asn Ala Ser Val Leu Ser
                245                 250                 255

Gly Phe Ala Phe Asn Asn Gly Gly Leu Gly Tyr Val His Ala Met Ala
            260                 265                 270

His Gln Leu Gly Gly Phe Tyr Asp Met Pro His Gly Ile Ala Asn Ala
        275                 280                 285

Ile Leu Leu Pro Tyr Val Glu Lys Phe Asn Leu Gly Thr Asp Val Glu
290                 295                 300

Arg Phe Ser Asn Ile Thr Glu Ile Phe Gly Lys Glu Gln Ser Lys Ile
305                 310                 315                 320

Ser Asn Asn Pro Glu Ala Gln Glu Ser Ile Lys Ala Ile Lys Asp Glu
                325                 330                 335

Ile Asp Lys Leu Lys Arg Phe Lys Ile Ala Glu Val Phe Gly Val
            340                 345                 350

Asp Thr Ser Asn Met Ser Thr Arg Glu Ala Ala Glu Ala Ser Leu Asp
        355                 360                 365

Ala Ile Lys Glu Leu Ala Arg Asp Ile Gly Ile Pro Ser Ser Leu Ser
370                 375                 380
```

```
Glu Ser Lys Phe Asp Val Lys Arg Asp Asp Phe Glu Glu Met Ala Lys
385                 390                 395                 400

Leu Ala Leu Glu Asp Gly Asn Ala Gly Thr Asn Pro Arg Lys Gly Ser
                405                 410                 415

Val Glu Asp Ile Val Arg Ile Phe Glu Asp Ala Phe
                420                 425
```